United States Patent [19]
Warner

[11] Patent Number: 5,947,895
[45] Date of Patent: Sep. 7, 1999

[54] ABDOMINAL RETRACTOR WITH ROTATING ARMS AND METHOD OF USING THE SAME

[75] Inventor: Robert D. Warner, Cupertino, Calif.

[73] Assignee: Origin Medsystems, Inc., Menlo Park, Calif.

[21] Appl. No.: 08/958,732

[22] Filed: Oct. 27, 1997

Related U.S. Application Data

[63] Continuation of application No. 08/485,499, Jun. 7, 1995, abandoned, which is a continuation-in-part of application No. 08/408,102, Mar. 21, 1995, abandoned, which is a continuation of application No. 08/128,477, Sep. 28, 1993, abandoned, which is a continuation-in-part of application No. 07/890,033, May 28, 1992, abandoned, which is a continuation-in-part of application No. 07/706,781, May 29, 1991, abandoned, and a continuation-in-part of application No. 08/062,707, May 18, 1993, Pat. No. 5,520,609, which is a continuation of application No. 07/706,781, May 29, 1991, abandoned.

[51] Int. Cl.⁶ ..................................................... A61B 17/02
[52] U.S. Cl. .......................... 600/204; 600/207; 600/225; 606/192; 606/198
[58] Field of Search ..................................... 600/204, 207, 600/214, 215, 225; 606/198, 192

[56] References Cited

U.S. PATENT DOCUMENTS

| | | |
|---|---|---|
| 1,798,124 | 3/1931 | Hunn .................................. 600/204 X |
| 2,841,148 | 7/1958 | Kadavy . |
| 4,165,746 | 8/1979 | Burgin ...................................... 81/302 |
| 4,744,363 | 5/1988 | Hasson . |
| 4,984,564 | 1/1991 | Yuen ....................................... 600/207 |
| 5,197,948 | 3/1993 | Ghodsian . |
| 5,345,927 | 9/1994 | Bonutti ................................... 600/207 |
| 5,381,788 | 1/1995 | Matula et al. . |
| 5,514,075 | 5/1996 | Moll et al. ........................... 600/204 X |
| 5,520,609 | 5/1996 | Moll et al. ............................... 600/204 |

FOREIGN PATENT DOCUMENTS 9114392  10/1991  WIPO ................................... 600/204

Primary Examiner—Michael H. Thaler
Attorney, Agent, or Firm—Limbach & Limbach LLP

[57] ABSTRACT

An apparatus and method for laparoscopically lifting the abdominal wall utilizes a pair of lifting rods each having a substantially straight proximal portion mounted to a lifting body and an arcuate distal portion joined to the proximal portion. The rods have an insertion configuration, in which their arcuate portions are nested such that the rods may be simultaneously extended into an abdominal cavity, and a lifting configuration in which one of the rods is pivoted such that the arcuate distal portions form a substantially circular lifting area between them. An inflatable balloon is disposed around the lifting arms and is inflated within the abdominal cavity to push abdominal tissue away from the abdominal cavity and to thereby prevent the tissue from catching on the lifting rods during pivoting.

16 Claims, 11 Drawing Sheets

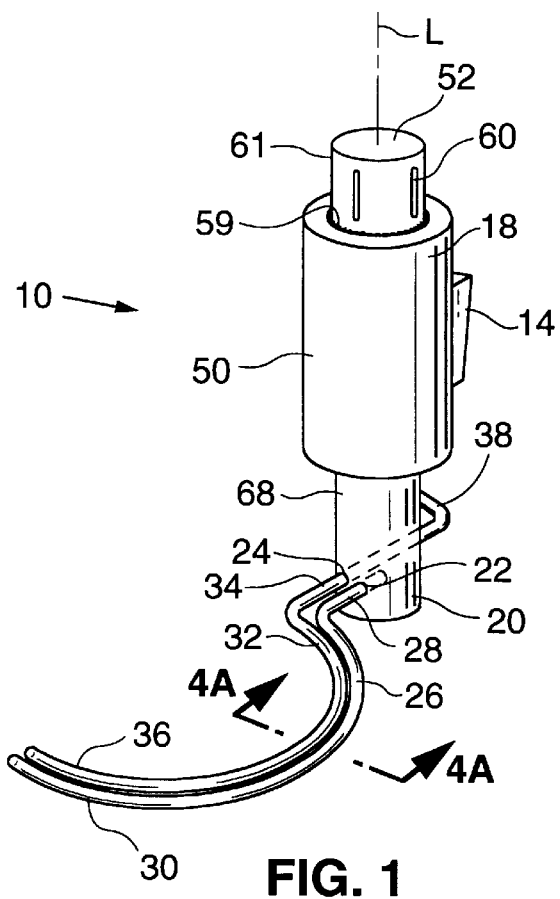
FIG. 1
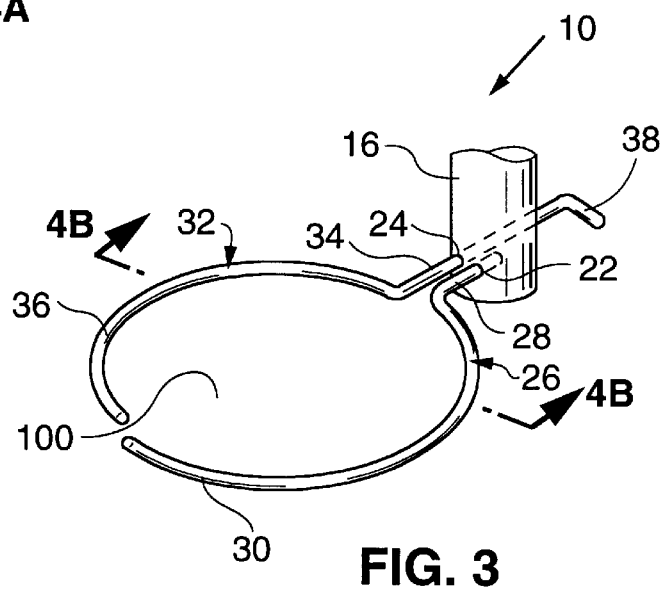
FIG. 3
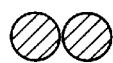
FIG. 4A
 
FIG. 4B

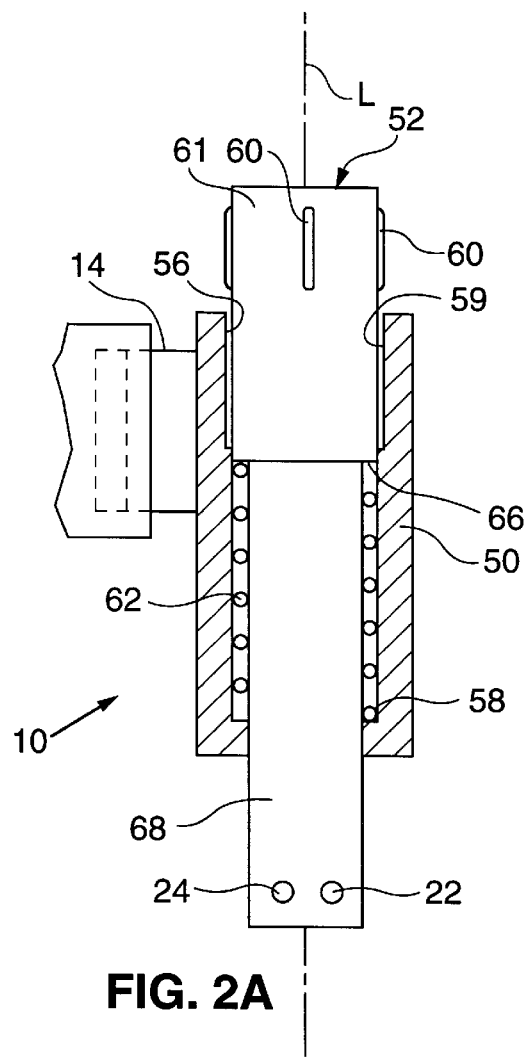
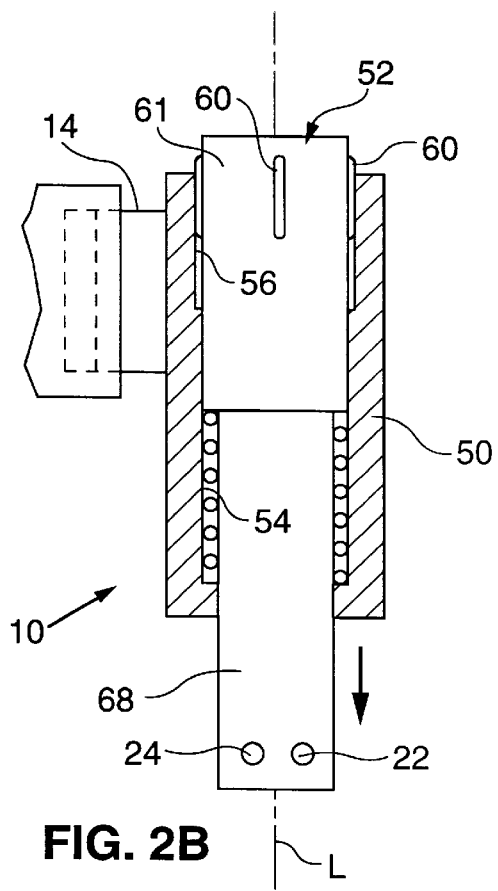
FIG. 2A
FIG. 2B

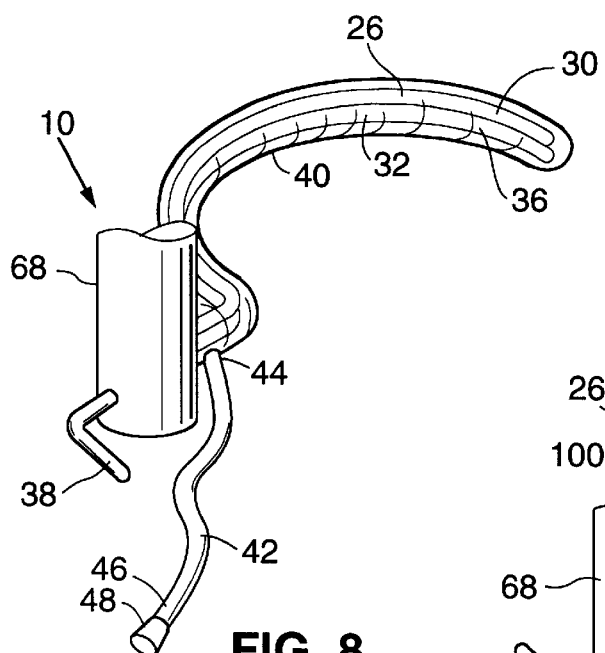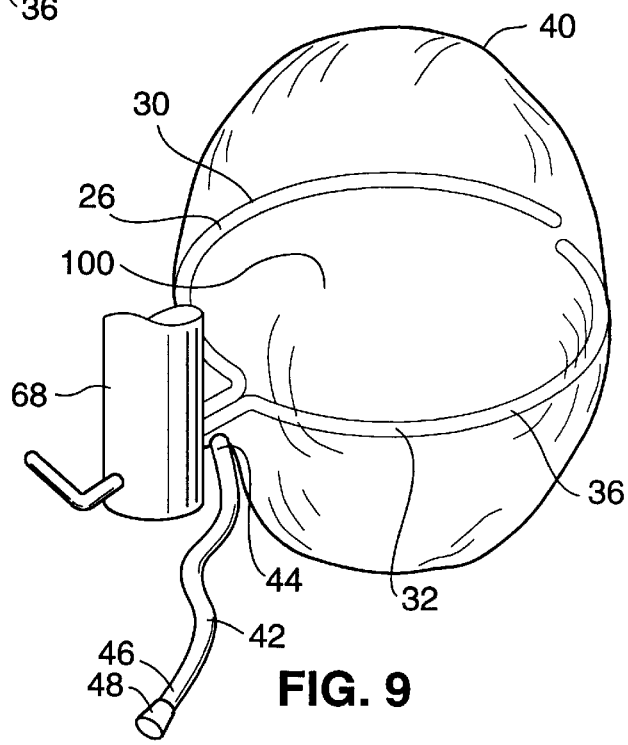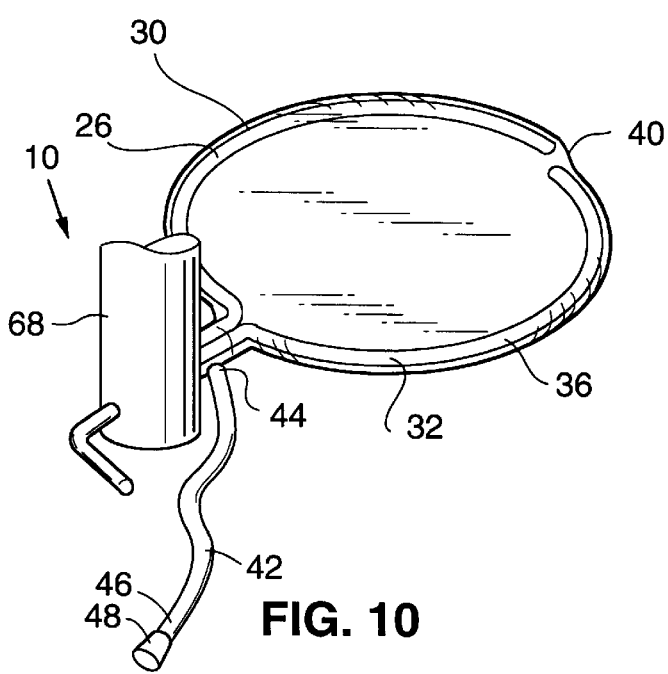

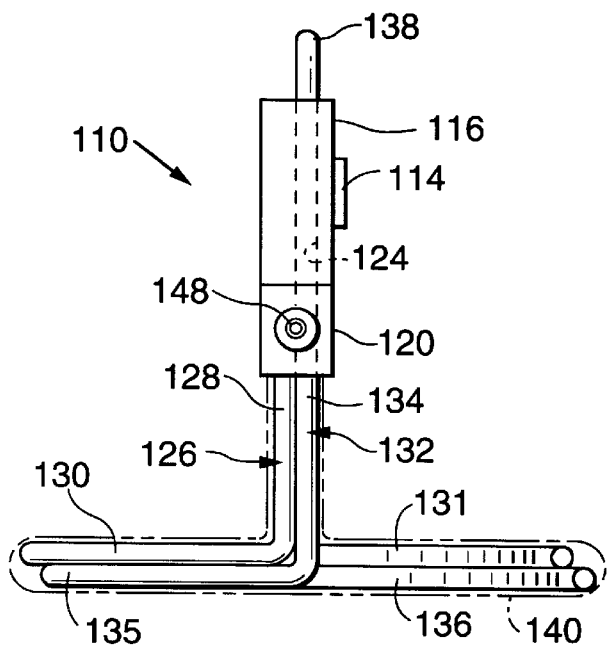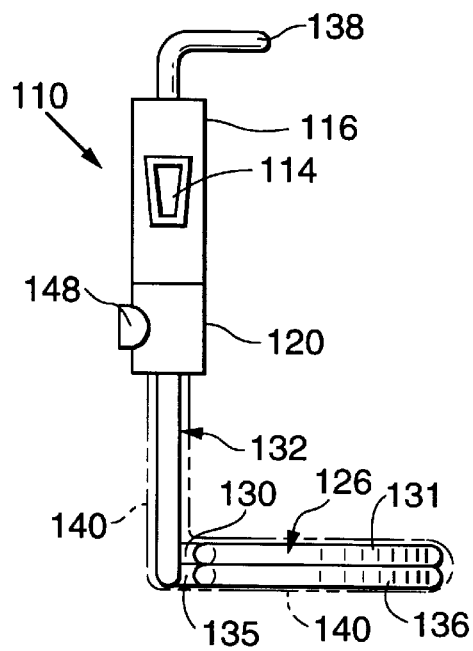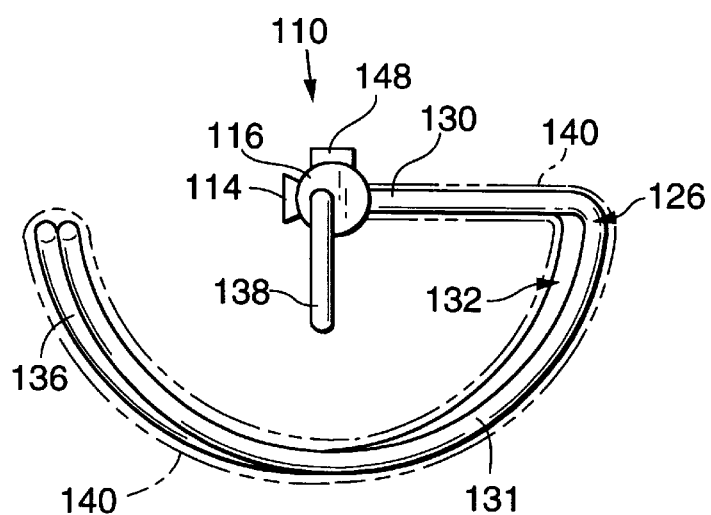

ABDOMINAL RETRACTOR WITH ROTATING ARMS AND METHOD OF USING THE SAME

This is a continuation of application Ser. No. 08/485,499 filed on Jun. 7, 1995, now abandoned, which is a continuation-in-part of Ser. No. 08/408,102 filed Mar. 21, 1995, now abandoned, which is a continuation of Ser. No. 08/128,477 filed Sep. 28, 1993, now abandoned, which is a continuation-in-part of Ser. No. 07/890,033 filed May 28, 1992, now abandoned, which is a continuation-in-part of Ser. No. 07/706,781 filed May 29, 1991 now abandoned, and a continuation-in-part of Ser. No. 08/062,707 filed May 18, 1993, now abandoned, which is a continuation of Ser. No. 07/706,781 filed May 29, 1991, now abandoned.

FIELD OF THE INVENTION

The present invention relates to the field of surgical retractors and particularly to lifting the abdominal wall during laparoscopic surgery.

BACKGROUND OF THE INVENTION

Laparoscopy dates back to the turn of the 20th Century. Early laparoscopic techniques were used primarily for diagnostic purposes to view the internal organs, without the necessity of conventional surgery. Since the 1930s, laparoscopy has been used for sterilization and, more recently, for suturing hernias. U.S. Pat. Nos. 4,919,152 and 4,944,443 are concerned with techniques for suturing hernias. Another recent innovation is the use of laparoscopic surgery for removing the gallbladder.

In the course of performing laparoscopic procedures in the abdomen, it is necessary to raise the abdominal wall to create space in which to work. A well-known method of raising the abdominal wall is to insufflate the abdominal cavity with a suitable insufflation gas, such as air, or carbon dioxide. A significant disadvantage of gas insufflation is that instruments must be passed into the abdominal cavity through gas-tight seals, which significantly reduce the surgeon's feel of the instruments.

Several mechanical alternatives to gas insufflation have been proposed. The Gazayerli Endoscopic Retractor Model 1, described in SURGICAL LAPAROSCOPY AND ENDOSCOPY, Vol. 1, No. 2, 1991, pages 98–100, has a rigid rod with a hinged blade at the distal end. The blade can rotate through 360 degrees about an axis perpendicular to the long axis of the rod. The blade is aligned with the long axis of the rod for insertion into the abdomen through a small puncture. Once inside the abdomen, the blade is swivelled through about 90 degrees to form a T-shaped structure. The proximal end of the rod can be raised by hand or by a rope, pulley and weight arrangement. Raising the rod causes the blade to engage the abdominal wall and to lift it.

French patent application no. 90-03980 shows a wire structure that is threaded into the abdomen through a small puncture to engage and to lift the abdominal wall. The application also shows a fan retractor that has a first angle-shaped member having a first leg that engages with the abdominal wall, a tubular second leg having a bore, and a third leg, remote from the first leg, that has a hook-shaped member on its end distal from the second leg. A second angle-shaped member has a first leg that engages with the abdominal wall, a second leg that pivots within the bore of the second leg of the first angle-shaped member, and a third leg, remote from the first leg, that serves as an operating lever for the second angle-shaped member. The first legs of the angle-shaped members are closed together to insert them into the abdominal cavity through an incision. The third leg of the second angle-shaped member is then operated to spread the first leg of the second angle-shaped member apart from the first leg of the first angle-shaped member. The first legs are engaged with the peritoneum inside the abdominal cavity. A lifting force is then applied to the hook-shaped member to lift the retractor and hence to lift the abdominal wall.

U.S. patent application Ser. No. 08/062,707, which is hereby incorporated by reference and which is one of the applications of which this application is a Continuation-in-Part, describes a number of different mechanical devices that are inserted through one or more punctures into the abdomen. All or part of the device is then lifted to lift the abdominal wall away from the underlying abdominal organs. One of the devices described in this application is a fan retractor having a pair of legs that are inserted in a closed condition into the abdomen, spread apart once inside the abdomen, and brought into contact with the peritoneum inside the abdomen. The fan retractor is then raised by a lifting arm to lift the abdominal wall. Other devices, such as those described in application Ser. Nos. 08/062,707, 07/891,228 and 07/877,995, which are hereby incorporated by reference, utilize an inflatable device which is introduced laparoscopically and, once in place, inflated to engage and lift an extensive area of the abdominal wall.

One disadvantage of present fan retractor systems is that the triangular lifting area provided by fan retractors is sometimes not sufficiently broad to allow visualization of a wide region of the abdominal cavity. Also, because these fan retractors utilize a pair of retraction rods which must be pivoted into retracting position, they pose the risk that the pivoting of the rods may be obstructed by surrounding tissue in the abdominal cavity. Additionally, abdominal tissue can sometimes drape between the legs of fan retractor, thereby obstructing the working space.

OBJECTS AND SUMMARY OF THE INVENTION

It is an object of the present invention to provide an apparatus and method for mechanically retracting the abdominal wall to provide visualization and working space. It is also an object of the present invention to provide an abdominal wall retraction system capable of lifting an area of abdominal wall that is greater than that which is provided using fan-shaped retractors. Another object of the present invention is to provide an abdominal wall retraction system having retractor arms which are capable of being inserted laparoscopically and pivoted relative to each other to create a lifting area while minimizing the likelihood that they will catch on surrounding tissue during pivoting. Still another object of the present invention is to provide a lifting retractor capable of minimizing caving of abdominal tissue into the working space provided by lifting.

The present invention is an apparatus and method for laparoscopically lifting the abdominal wall. It utilizes a pair of lifting rods each having a substantially straight proximal portion mounted to a lifting body and an arcuate distal portion joined to the proximal portion. The rods have an insertion configuration, in which their arcuate portions are is side by side relation such that the rods may be simultaneously extended into an abdominal cavity, and a lifting configuration in which one of the rods is pivoted such that the arcuate distal portions form a substantially circular lifting area between them. An inflatable balloon is disposed around the lifting arms and is inflated within the abdominal cavity to push abdominal tissue away from the abdominal cavity and to thereby prevent the tissue from catching on the lifting rods during pivoting.

BRIEF DESCRIPTION OF THE DRAWINGS

FIG. 1 is a perspective view of a first exemplary embodiment of a lifting retractor according to the present invention, with the balloon not shown, showing the lifting rods in the closed position.

FIGS. 2A and 2B are partial cross-sectional front views of the cylindrical lifting body of the embodiment of FIG. 1, showing the lifting body in the unloaded and loaded conditions, respectively.

FIG. 3 is a partial perspective view of the lifting retractor of FIG. 1 showing the lifting rods in the open, lifting, position.

FIGS. 4A and 4B are cross-section views of the lifting rods of the lifting retractor of FIG. 1, taken along the planes designated 4A—4A and 4B—4B in FIGS. 1 and 3, respectively.

FIG. 8 is a partial perspective view of the lifting retractor of FIG. 1, with the balloon in place, showing the lifting rods in the closed position.

FIG. 9 is a partial perspective view of the lifting retractor of FIG. 1, showing the lifting rods in the lifting position with the balloon inflated.

FIG. 10 is a partial perspective view of the exemplary embodiment of a lifting retractor according to the present invention showing the lifting rods in the lifting position with the balloon deflated.

FIG. 14 is a side elevational view of a second exemplary embodiment of a lifting retractor according to the present invention.

FIG. 15 is a front elevational view of the lifting retractor of FIG. 14.

FIG. 16 is a top plan view of the lifting retractor of FIG. 14.

DESCRIPTION OF THE EXEMPLARY EMBODIMENTS

First Exemplary Embodiment

Structure

Figure 5:
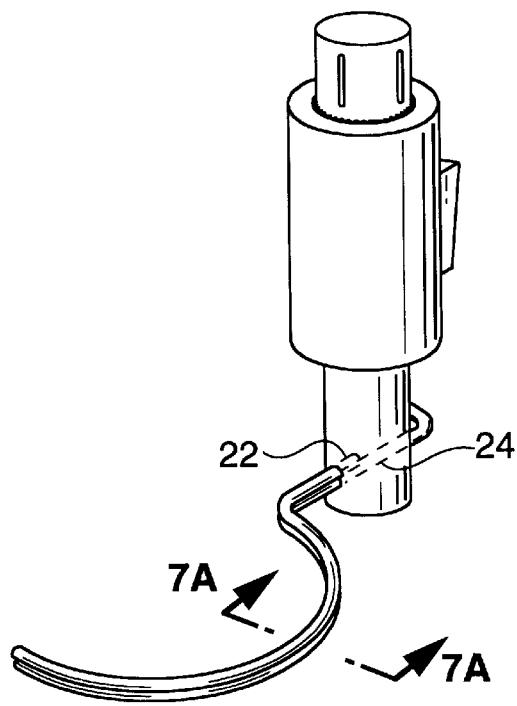
FIGS. 5 and 6 are a perspective view and a partial perspective view, respectively, of a modification of the lifting retractor of FIG. 1, showing the lifting rods oriented vertically of one another and further showing the rods having "D"-shaped cross-sections.
Figure 6:
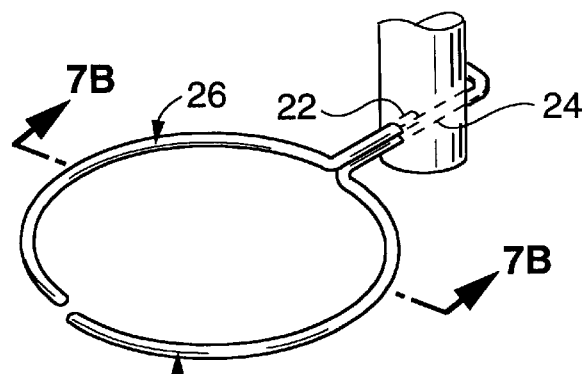

As shown in FIG. 1, the first exemplary embodiment of a lifting retractor according to the present invention is comprised generally of a lifting body 10 and a pair of lifting rods 26, 32. A dovetail connector 14 is attached to the lifting body 10 which allows the apparatus to be mounted to a mechanical lifting arm such as the one designated 200 in FIG. 12 and described in application Ser. No. 07/959,717, which is incorporated herein by reference.

Referring to FIGS. 2A and 2B, the lifting body 10 is comprised of a tubular section 50 and a keyed column 52 slidably received within the section 50. The tubular section 50 is formed with a throughbore 54 having a proximal portion 56 having spaced splines 59 formed along its surface. A shoulder 58 is formed in the throughbore 54 at the distal end of the tubular section 50. A compression spring 62 is positioned within the throughbore 54 and rests on the shoulder 58. The dovetail mount 14 is connected to the exterior of the splined tubular section 50 for attachment to a mechanical lifting arm such as the one designated 200 in FIG. 12.

The keyed column 52 of the lifting body 10 is comprised of a proximal section 61 and a distal section 68. The distal section 68 has a smaller diameter than the proximal section 61 and a shoulder 66 is formed between the proximal section 61 and the distal section 68. Spaced keys 60 are positioned on the proximal section 61 of the column 52.

Bores 22, 24 are formed in the distal section 68 of the column 52. The bores 22, 24 may be positioned laterally of one another as shown in FIGS. 1, 2A and 2B. They may also be positioned one above the other as in FIGS. 5 through 7B or in any other configuration in which they are located substantially close together.

As shown in FIGS. 2A and 2B, the keyed column 52 is proportioned to fit slidably inside the throughbore 54 of the tubular section 50 with the compression spring 62 disposed around distal section 68. The proximal section 61 of the column 52 is positioned proximally of the compression spring 62 with the shoulder 66 resting on the compression spring 62.

The configuration of the lifting body 10 facilitates positioning of the rods 26, 32 prior to lifting by enabling rotation of the rods around the longitudinal axis of the lifting body. It also prevents the rods from rotating once the rotational position of the rods has been selected and a lifting force applied.

When the apparatus is in an unloaded state, the compression spring 62 holds the column 52 in an elevated condition such that the keys 60 are disengaged from the splines 59 as shown in FIG. 2A. When in this state, the keyed column 52 is capable of rotating about its longitudinal axis while the tubular section 50 remains fixed. This allows the rods 26, 32, which as shown in FIG. 1 are disposed within the bores 22, 24 in the column 52, to be rotated around the longitudinal axis, designated L, of the keyed column 52 and into a desired position within an abdominal cavity.

When tensile force is applied between the splined tubular section 50 and the rods 26, 32, the rods pull the keyed column 52 such that it moves longitudinally within the throughbore 54 in the distal direction (indicated by an arrow in FIG. 2B) thereby causing the shoulder 66 to depress the spring 62. When the column advances sufficiently far within the throughbore 54 for the keys 60 to enter the throughbore, the keys engage with the splines 59. Engagement of the splines 59 and the keys 60 locks the column 52 and the section 50 against further rotation of the keyed column 52 and thus aids in preventing the rods 26, 32 from moving out of the chosen position during lifting. The spring 62 is preferably one having a spring constant that will resist engagement of the keys 60 and splines 59 until the tensile load reaches approximately five pounds.

Referring to FIG. 1, the lifting rods 26, 32 engage in the bores 22, 24 formed in the lifting body 10. Rod 26 is a fixed rod having a straight proximal section 28 secured within bore 22 and extending from the bore substantially normally of the lifting body 10. An arcuate distal section 30 extends laterally of straight section 28 of rod 26.

The other of the rods, designated 32, has a straight proximal section 34 rotatably disposed within bore 24 and an arcuate distal section 36 extending laterally of straight section 34. Connected to the proximal end of rotatable rod 32, on the opposite side of the lifting body 10 from the arcuate distal section 36, is a lever 38. Rotatable rod 32 is configured such that when it is rotated around the longitudinal axis of straight section 34, using lever 38, its arcuate distal section 36 pivots around straight proximal section 34.

The lifting rods 26, 32 are configured so that their arcuate distal sections 30, 36 are nested when rotatable rod 32 is in the closed position shown in FIG. 1, and such that the arcuate distal sections 30, 36 form the substantially round lifting area, designated 100 in FIG. 3, when rotatable rod 32 is pivoted into the open position as shown. A locking mechanism (not shown) is provided for locking the rod 32 in the open position. Of course, the lifting area 100 can be made to have many different shapes by providing lifting rods 26, 32 having distal sections 30, 36 formed into configurations other than the arcuate configurations shown in the drawings. For example, the distal sections 30, 36 may be made to be angular in order to form a trapezoidal lifting area. For the purposes of this application, the term "arcuate" is not limited to configurations defining an arc of a circle, but instead is intended to include any configuration having an arc or bend intermediate of its proximal and distal ends.

Figure 7A:
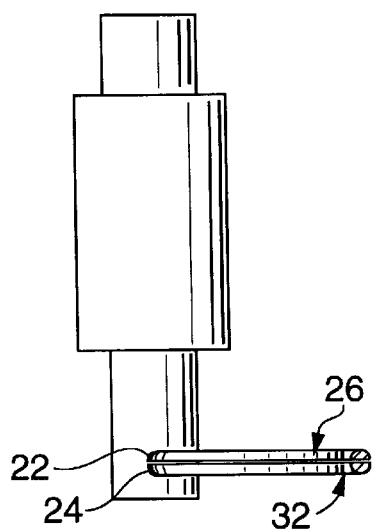
FIGS. 7A and 7B are front elevational views of the lifting retractor of FIGS. 5 and 6, showing the lifting rods in cross-section.
Figure 7B:
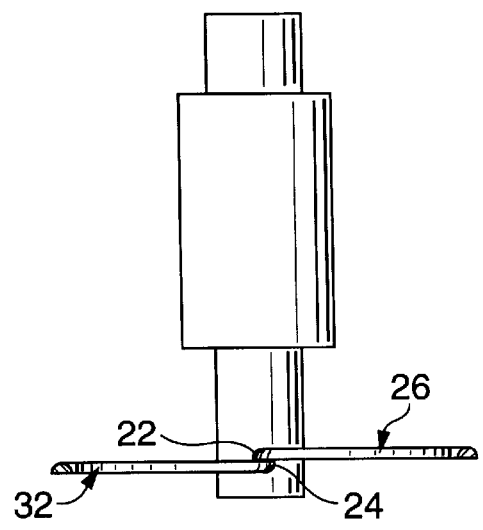

Because the abdominal wall tissue may be traumatized if blunt-edged rods are used for lifting, the cross-sectional shape of the rods is preferably free of blunt edges or corners so as to minimize such trauma. The rods may be circular in cross-section as shown in FIGS. 4A and 4B, or they may have an elliptical or other rounded cross-section. The rods may also be formed having "D"-shaped cross sections as shown in FIGS. 7A and 7B and configured such that when the rods are in the nested configuration the flat sides of the "D"'s are flush with each other and such that when in the open position the rounded sides are positioned against the abdominal wall for lifting. If rods with "D"-shaped cross-sections are used, it is preferable to have the bore 22a substantially vertical of bore 24a. When the rods are in the open position the rounded portions of their respective cross-sections are thereby in position for contacting the upper abdominal wall BB (See FIG. 13). The rods are also designed such that they will deform slightly downwards during lifting to conform to the shape of the raised abdomen and to thereby distribute the weight of the abdominal wall along the length of the rods.

An inflatable balloon 40 (not shown in FIGS. 1 and 3) is sealed around the arcuate distal sections 30, 36 of the lifting rods 26, 32. The balloon may be manufactured out of an elastomeric material such as latex or silicone, a non-elastomeric material such as polyethylene, teflon, or polyvinyl, or a combination of elastomeric and non-elastomeric materials.

An elastic balloon is shown in FIGS. 8 through 10. If an elastomeric material is used, the material will stretch between the distal portions of the rods when the rods are in the open position to form a taut membrane between the rods as shown in FIG. 10.

The balloon 40 is provided with an inflation tube 42 having a distal end 44 connected to the balloon 40 and a proximal end 46 provided with a valve 48. The inflation tube 42 has a passageway that is contiguous with the interior of the balloon 40 so as to allow an inflation medium, such as air, to be introduced into or released from the balloon via the inflation tube 42 when the valve 48 is opened.

Figure 11A:
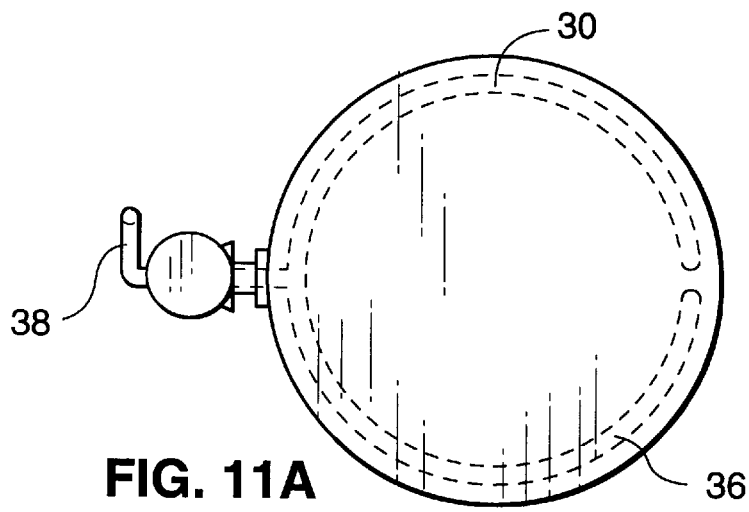
FIGS. 11A–11C are a top plan view, a side elevational view, and a front elevational view of the lifting retractor of FIG. 1, showing the lifting rods in the lifting position and further showing an alternative balloon inflated around the lifting rods.
Figure 11B:
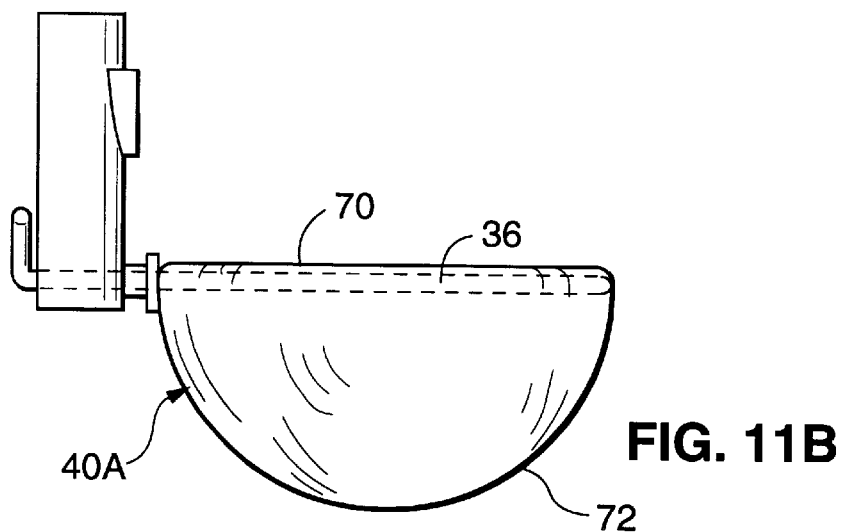
Figure 11C:
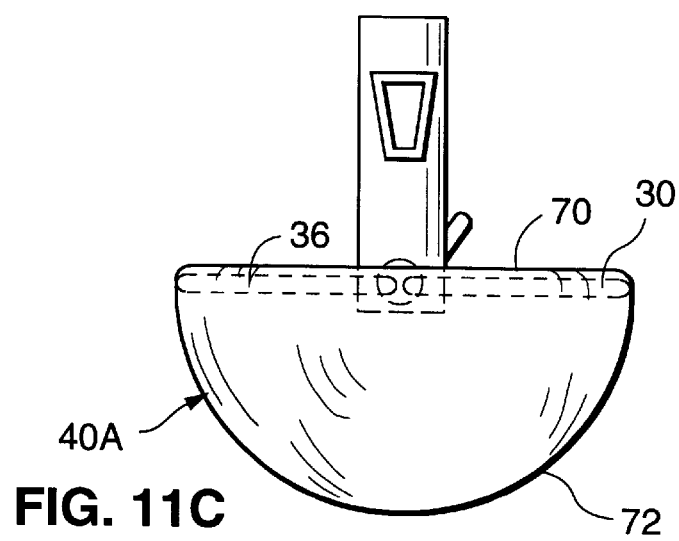

One type of non-elastic balloon 40a which may be used with the present invention is shown in FIGS. 11A through 11C. This balloon 40a is comprised of a flat side 70 and a substantially hemi-spherical portion 72. It is disposed around the rods such that its flat side 70 extends between the arcuate distal portions 30, 36 of the lifting rods when the rods are in the open position and such that the hemi-spherical portion 72 extends downwardly into the abdominal cavity during use. When the rods are in the open position, the flat side 70 is held taut by the arcuate distal portions 30, 36 of the lifting rods to prevent draping of abdominal tissue between the rods. When the balloon is not inflated, the hemi-spherical portion 72 may be prevented from hanging into the abdominal working space by applying suction to the inflation tube (which is similar to the inflation tube 42 of FIG. 10). The balloon 40a may alternatively be covered with an elastomeric material so that the hemi-spherical portion 72 of the balloon 40a will retract towards the rods and thus away from the working space when the balloon is not inflated.

A semi-structural balloon (not shown) may be alternatively be employed for creating a space for movement of the rotatable lifting rod 32. A balloon of this type may be provided to have working channels or tunnels, so that the balloon may be left inflated during use while still provide a passageway through which instruments may be inserted in order to gain access to the surgical working space. Semi-structural balloons of this type are shown and described in application Ser. No. 08/134,573, which is incorporated herein by reference.

Operation

Prior to insertion, the rotatable rod 32 is pivoted into the nested insertion configuration shown in FIG. 8. The side-by-side relationship of the arcuate distal sections 30, 36 allows for easy insertion of the lifting rods 26, 32 into an abdominal cavity CC through a puncture opening AA formed in an abdominal wall BB (see FIG. 12). The arcuate distal sections 30, 36 are introduced through the puncture opening AA using a hooking motion and the lifting body 10 is connected to the mechanical lifting arm 200 using dovetail connector 14.

The valve 48 of the inflation tube 42 (not shown in FIG. 12) is next opened and an inflation medium, such as air, is introduced through the inflation tube 42 into the balloon 40. The inflating balloon displaces organs and tissue DD surrounding the lifting rods 26, 32 so as to form a cavity through which rod 32 can pivot.

Figure 12:
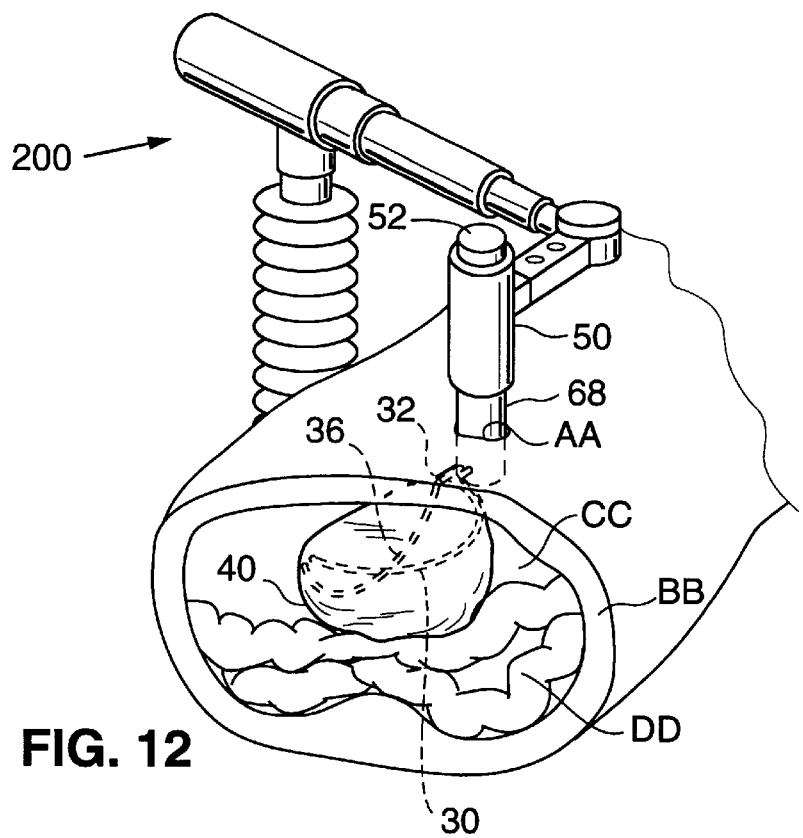
FIG. 12 is a perspective view of the lifting retractor of the embodiment of FIG. 1 showing the balloon inflated for deployment of the rods within an abdominal cavity and showing the rotatable lifting rod pivoting from the closed to the open position within the abdominal cavity.
Figure 13:
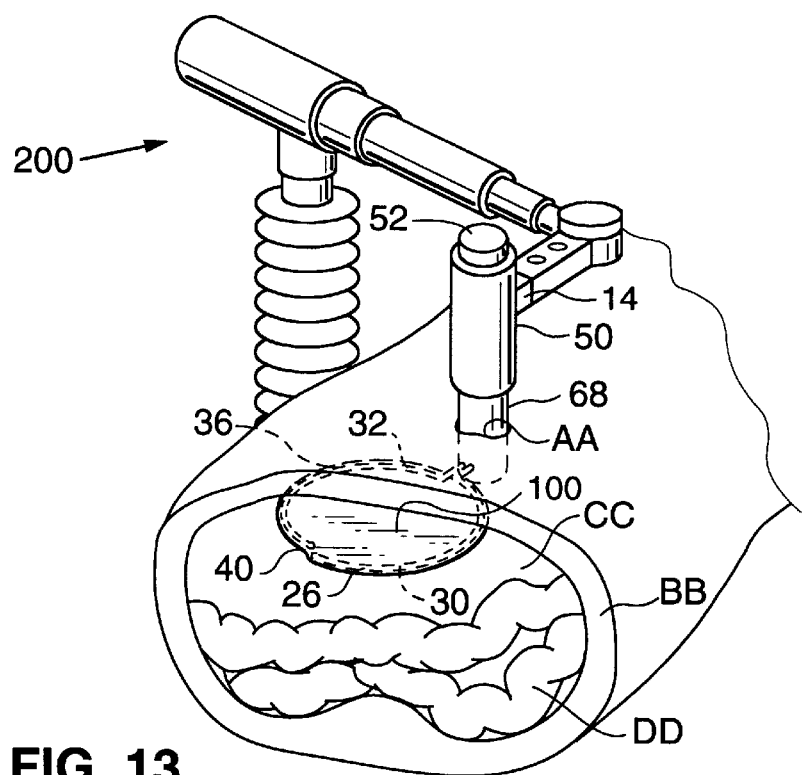
FIG. 13 is a perspective view of the lifting retractor of FIG. 1 showing the lifting rods in the deployed position for lifting within an abdominal cavity and the balloon deflated for support of the abdominal wall within the perimeter of the lifting rods.

As shown in FIG. 12, rod 32 is next pivoted 180° into the open lifting configuration such that the arcuate distal sections 30, 36 of the lifting rods 26, 32 form the substantially round lifting area 100 shown in FIG. 13. The rod 32 is locked into the lifting position using a locking mechanism (not shown). The valve 48 is next opened and the balloon 40 is allowed to deflate. The deflated balloon, which is held taut by the arcuate distal sections 30, 36 of the lifting rods 26, 32 in their lifting configuration, serves as a support surface which assists in lifting the abdominal wall and which prevents abdominal tissue from draping between the lifting rods 26, 32 into the surgical working space. If a nonelastomeric balloon 40a such as the one shown FIG. 11A–11C is utilized, suction may be applied to the inflation tube (not shown) connected to the balloon 40a so as to draw hemi-spherical portion 72 close to the rods 26, 32 and to thereby prevent it from obstructing the working space formed in the abdominal cavity.

If desired, the rods 26, 32 may be repositioned by rotating distal portion 68 of keyed column 52 relative to tubular section 50. Once the rods 26, 32 are in the desired position, the lifting body 10 is raised by the mechanical lifting arm 200 and thus lifts the abdominal wall BB. Lifting causes longitudinal movement of column 52 within tubular section 50 and thereby locks the rods in the desired position within the abdominal cavity CC by causing the keys 60 and splines 59 (see FIG. 2B) to engage.

To remove the apparatus from the abdominal cavity, the lifting arm 200 is lowered and the balloon 40 is inflated as described above. Rod 32 is next rotated 180° to place the rods 26, 32 in the nested configuration shown in FIG. 1. The balloon is subsequently deflated and the rods 26, 32 are removed from the abdominal cavity CC. Also, the pivoting rod 32 may be rotated to the nested position with rod 26 while the abdominal wall is raised without the balloon being required as the organs and tissue will be sufficiently far enough away as to cause no obstruction of the pivoting rod. This might be preferred as the deflated balloon may have been punctured by tools or instruments during the procedure.

Second Exemplary Embodiment

Structure

A second embodiment of a lifting retractor 110 according to the present invention is shown in FIGS. 14 through 16. The second embodiment is comprised generally of a cylindrical lifting body 116 which may be provided with components similar to those shown in FIGS. 2A and 2B and described with respect to the first exemplary embodiment. The second embodiment further comprises a pair of lifting rods 126, 132, and an inflatable balloon 140 disposed around the lifting rods 126, 132. For purposes of clarity, the balloon 140 is shown in dashed lines in FIGS. 14–16.

Referring to FIG. 14, lifting rod 126 has a substantially straight proximal portion 128 fixed to and extending longitudinally from distal end 120 of the lifting body 116. A substantially straight intermediate portion 130 of the rod 126 extends substantially laterally of the proximal portion 128, and an arcuate distal portion 131 (best shown in FIG. 16) extends substantially laterally of the intermediate portion 130. The other of the rods, designated 132, has a substantially straight proximal section 134 rotatably disposed within a bore 124 in the cylindrical body 116 and extending substantially longitudinally from the cylindrical body 116. An intermediate section 135 extends substantially laterally of proximal section 134, and an arcuate distal section 136 extends substantially laterally of intermediate section 135. Connected to the proximal end of rotatable rod 132, on the opposite side of the lifting body 116 from the arcuate distal section 136, is a lever 138. Rotatable rod 132 is configured such that when it is rotated around the longitudinal axis of straight section 134, using lever 138, its arcuate distal section 136 pivots around straight proximal section 134.

Figure 20A:
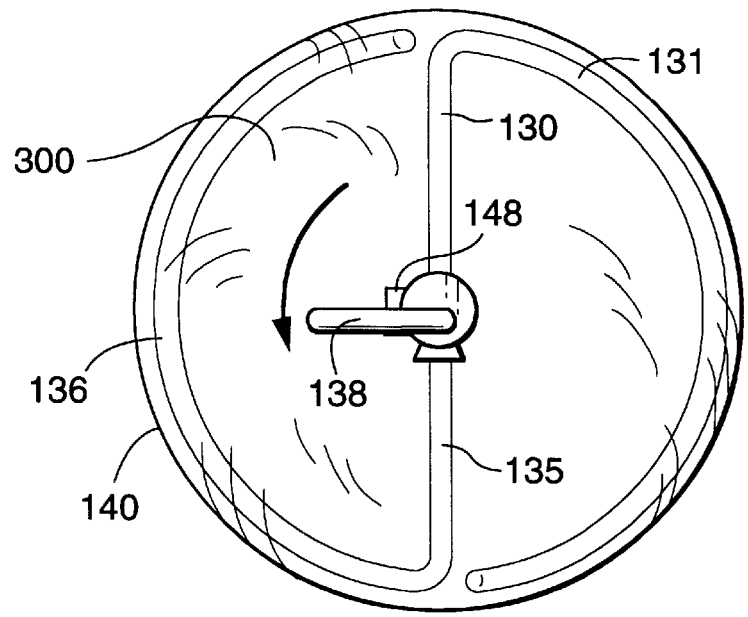
FIGS. 20A and 20B are a top plan view and a front elevational view, respectively, showing the lifting retractor of FIG. 14 with the balloon inflated and the lifting rods in the lifting configuration.
Figure 20B:
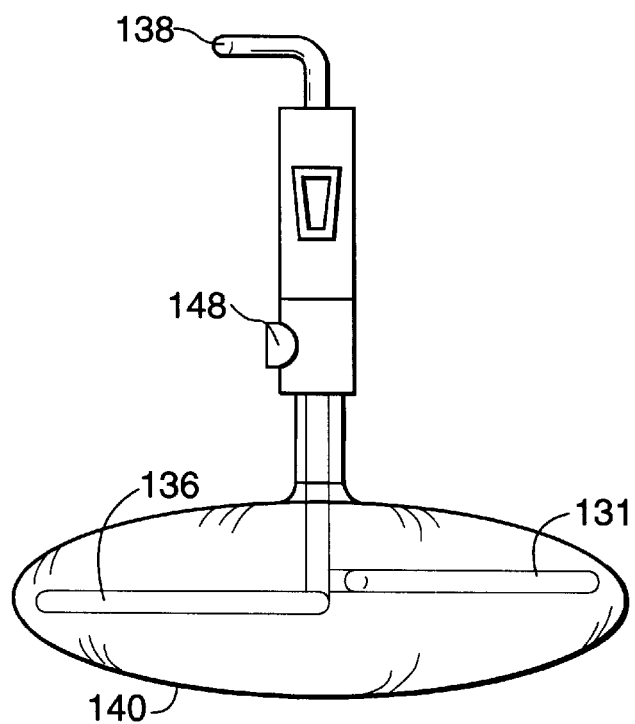
Figure 21A:
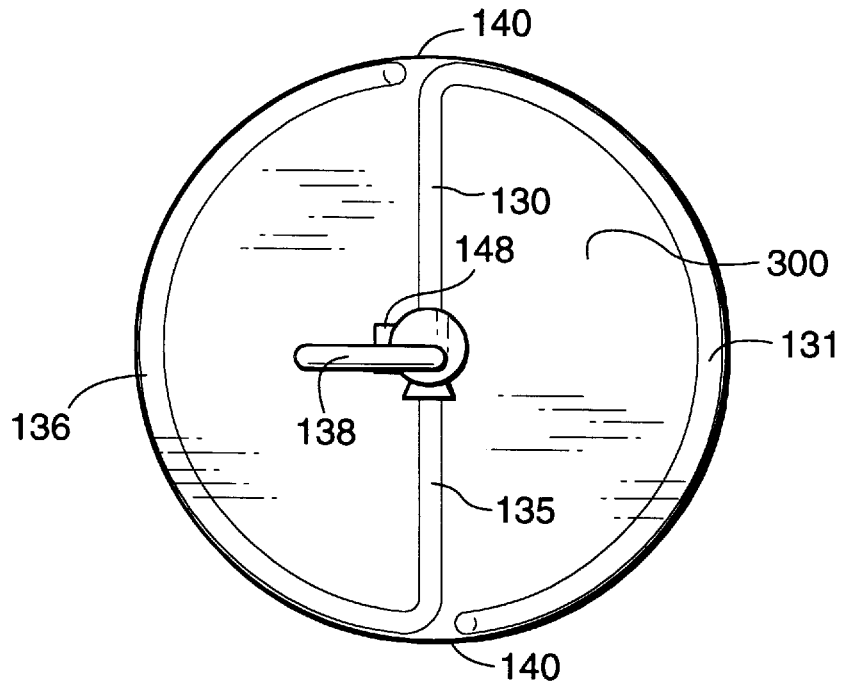
FIGS. 21A and 21B are a top plan view and a front elevational view, respectively, showing the lifting retractor of FIG. 14 with the balloon deflated and the lifting rods in the lifting configuration.

The lifting rods 126, 132 are configured so that their arcuate distal sections 131, 136 are nested when rotatable rod 132 is in the closed position shown in FIGS. 14–16, and such that the arcuate distal sections 131, 136 form the substantially round lifting area, designated 300 in FIGS. 20A and 21A when rotatable rod 132 is pivoted into the open position (see FIG. 20A). A locking mechanism (not shown) is preferably provided for locking the rod 132 in the open position. The rods are preferably free of blunt edges which could traumatize tissue during lifting. The rods 126, 132 may be formed to have the elliptical or D-shaped crosssections shown in FIGS. 4A and 7A.

The balloon 140 extends from distal end 120 of the lifting body 116. The balloon 140 may be constructed of one of a variety of different materials, including but not limited to those described with respect to the first exemplary embodiment.

An inflation port 148 having a valve (not shown) is formed in the lifting body 116, near the distal end. The inflation port 148 is contiguous with a passageway (not shown) which extends through the lifting body 116 between the inflation port 148 and the balloon 140 so as to allow an inflation medium, such as air, to be introduced into or released from the balloon via the inflation port 148.

Operation

Operation of the second embodiment will be described with reference to FIGS. 17A through 21B. After the arcuate portions 131, 136 of the lifting rods 126, 132 are inserted through a laparoscopic puncture and positioned within the abdominal cavity (not shown), the lifting body 116 is mounted, via the dovetail connector 114, to a mechanical lifting arm such as the one designated 200 in FIG. 12. An inflation medium is next introduced via the inflation port 148 to inflate the balloon 140 to the inflated state shown in FIGS. 17A and 17B. The inflating balloon displaces organs and tissue surrounding the lifting rods 126, 132 so as to form a cavity through which rod 132 can rotate without snagging on surrounding tissue.

Figure 17A:
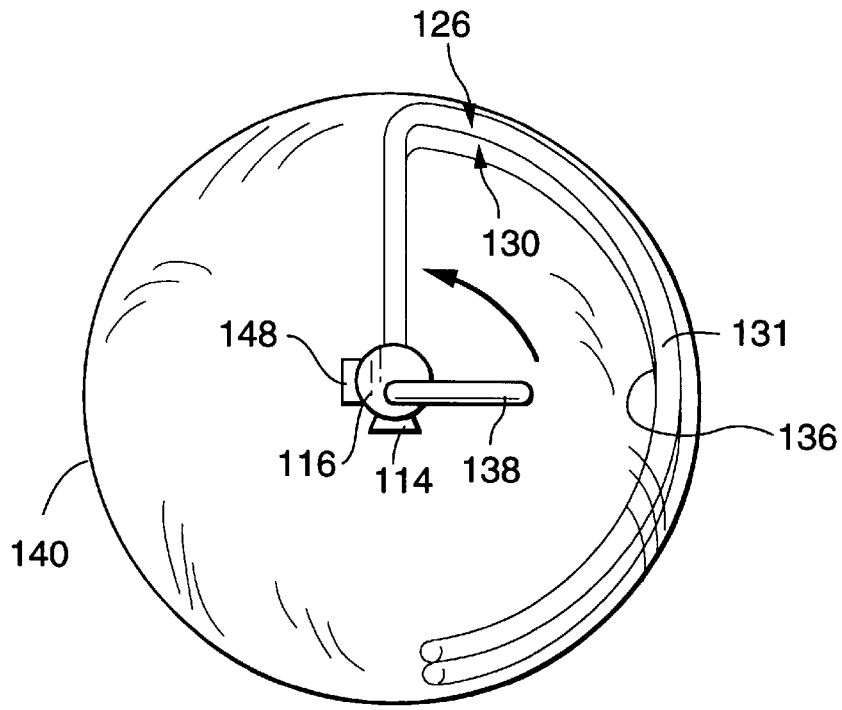
FIGS. 17A and 17B are a top plan view and a front elevational view, respectively, showing the lifting retractor of FIG. 14 with the balloon inflated.
Figure 17B:
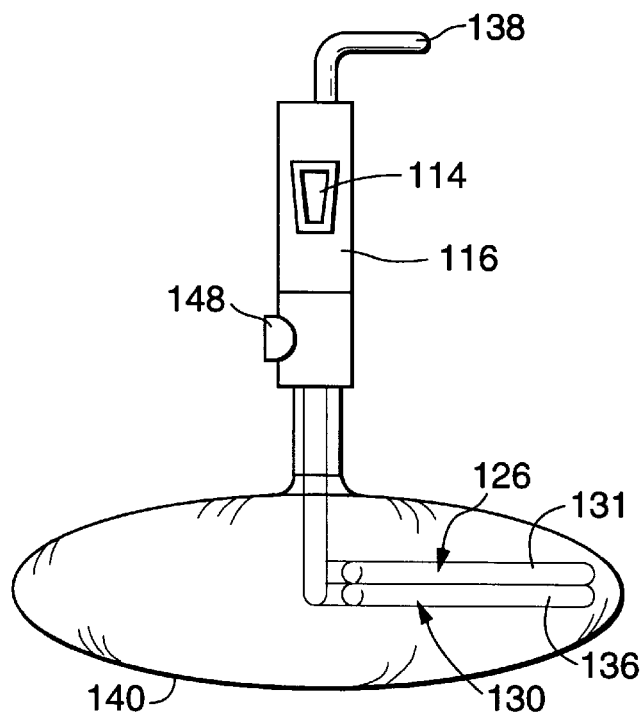
Figure 18:
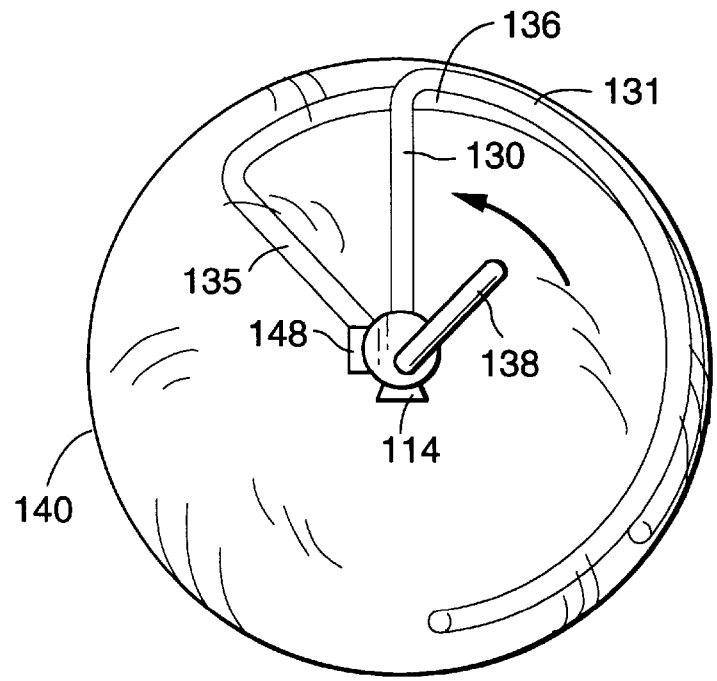
FIGS. 18 and 19 are top plan views of the lifting retractor of FIG. 14 showing the rotatable lifting rod being rotated into the lifting configuration.
Figure 19:
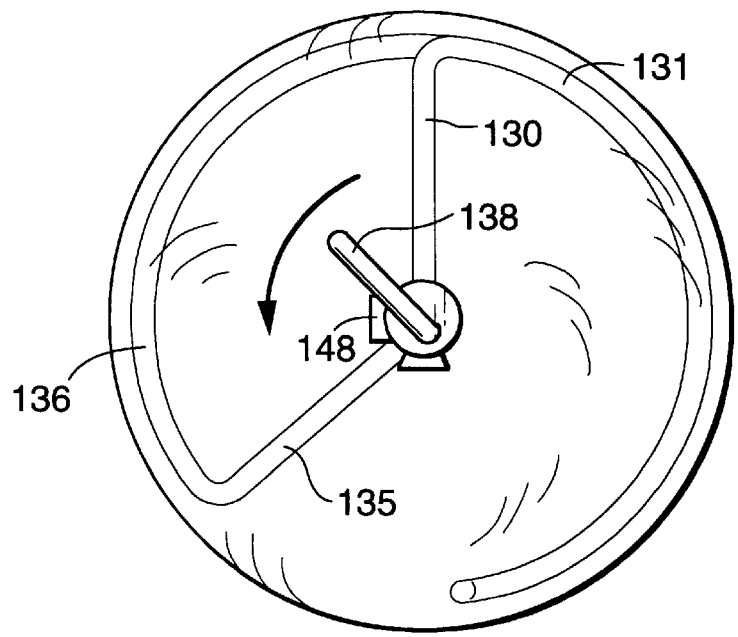

After the balloon 140 is inflated, lever 138 is rotated in the direction shown in FIG. 17A, causing the lifting rod 132 to rotate within the throughbore 124 (FIG. 14) as shown in FIGS. 17A through 20B. When the lever has been rotated through an angle of approximately 180°, the intermediate portions 130, 135 of the lifting rods 126, 132 are separated by a rotational angle of 180° and the arcuate portions 131, 136 of the lifting rods 126, 132 form the substantially round lifting area designated 300 in FIG. 20A.

Figure 21B:
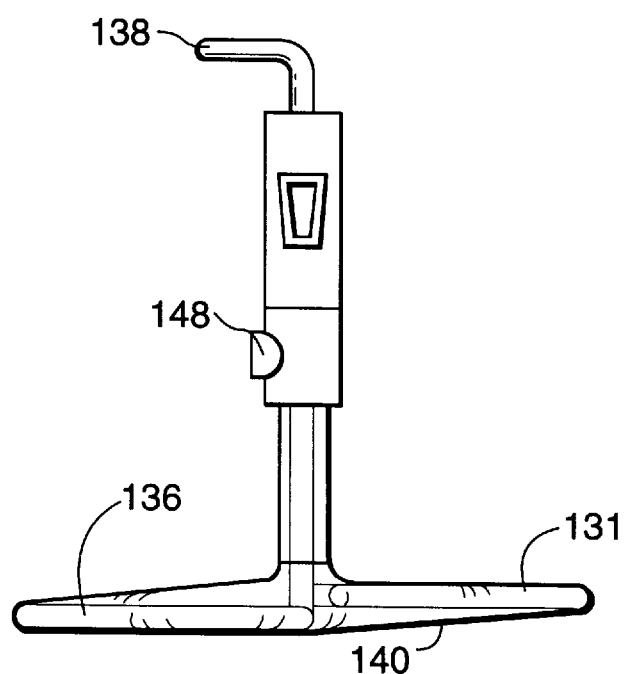

Next, the inflation medium is released from the balloon 140 via inflation port 148, to cause the balloon 140 to deflate into the deflated state shown in FIGS. 21A and 21B. The deflated balloon 140, which is held taut by the arcuate distal sections 131, 136 of the lifting rods 126, 132 in their lifting configuration, serves as a support surface which assists in lifting the abdominal wall and which prevents abdominal tissue from draping between the lifting rods 126, 132 into the surgical working space.

The two exemplary embodiments just described utilize inflatable balloons which are inflated prior to deployment of the rotatable rod in order to create sufficient space within the abdominal cavity for the rotatable rod to be rotated without snagging surrounding tissue. It should be appreciated that other means for creating a space for deployment of the rotatable rod may be utilized within the scope of the present invention. For example, auxilliary devices for at least partially lifting the abdominal wall and/or for retracting tissue surrounding the lifting rods may be used to clear an area for rotation of the rotatable rod.

Conclusion

While the present invention has been described with respect to a specific embodiment, it will be appreciated that additional embodiments may be created that fall within the scope of the present invention. The invention is not intended to be limited by the specifics of the embodiment which has been illustrated and described, but is limited only in terms of the accompanying claims.

I claim:

1. An apparatus for lifting a body wall, the apparatus comprising:
   a lifting body;
   a plurality of lifting rods mounted to the lifting body for relative movement between an insertion configuration, wherein the rods are configured for simultaneous insertion into and withdrawal from a body cavity through an opening in the body wall, and a lifting configuration wherein the rods are spaced to define a lifting area between them, the lifting rods including
      first and second lifting rods each having a proximal section carried by the lifting body, and a distal section extending laterally of the proximal section in a fixed position relative to the proximal section, the distal section including a distal tip and an intermediate section between the proximal section and the distal tip wherein in the insertion configuration the lifting rods are positioned with the distal sections in side by side relationship and in the lifting configuration the intermediate sections are spaced from one another such that the outermost portions of the intermediate sections are further apart from one another than the distal tips are from one another;
   balloon means inflatable within the abdominal cavity for pushing abdominal tissue away from the rods to facilitate movement of the rods between the insertion and lifting configurations; and
   means for delivering a lifting force to the lifting body.

2. The apparatus of claim 1 wherein at least one of the lifting rods is longitudinally rotatable between the insertion configuration and the lifting configuration.

3. The apparatus of claim 1 wherein at least one of the distal sections is slidable relative to the other of the distal sections into the lifting configuration.

4. The apparatus of claim 1 wherein the balloon means comprises an inflatable balloon disposed around at least one of the lifting rods.

5. The apparatus of claim 4 wherein the balloon is disposed around the first and second lifting rods and forms a supporting membrane surface between the first and second lifting rods when the rods are in the lifting configuration and the balloon deflated.

6. The apparatus of claim 4 wherein the balloon is disposed around the first and second lifting rods and is in tension between the first and second lifting rods when the rods are in the lifting configuration and the balloon is deflated.

7. The apparatus of claim 1 wherein:
   the lifting body further comprises:
      a first body portion and a second body portion joined for relative rotational movement, the lifting rods mounted to the second body portion; and
      locking means for preventing relative rotational movement of the first and second body portions when an excess of a predetermined loading force is delivered to the lifting rods.

8. In a retractor device for lifting a body wall wherein the retractor device is of the type having a lifting body and a plurality of rods extending from the lifting body and being capable of relative movement within a body cavity between an insertion configuration and a lifting configuration, the improvement comprising:
   lifting rods including first and second rods each having a proximal section connected to the lifting body, and a distal section extending laterally of the proximal section in a fixed position relative to the proximal section, the distal section including a distal tip and an intermediate section between the proximal section and the distal tip wherein in the insertion configuration the rods are positioned with the distal sections in side by side relationship and in the lifting configuration the intermediate sections of the rods are spaced from one another to define a lifting plane between them and the distal tips are proximal to one another, at least one of the intermediate sections rotatable out of the lifting plane to alter the rods between the insertion and lifting configurations; and
   balloon means inflatable within the abdominal cavity for pushing body tissue away from the rods to facilitate movement of the rods between the insertion and lifting configurations.

9. The improvement of claim 8 wherein the balloon means comprises an inflatable balloon disposed around at least one of the lifting rods.

10. The improvement of claim 9 wherein the balloon is disposed around the first and second lifting rods and is proportioned such that the balloon extends between the rods when the rods are in the lifting configuration.

11. The improvement of claim 8 wherein the balloon disposed around the first and second lifting rods and is in tension between the rods when the rods are in the lifting configuration and the balloon is deflated.

12. A method of lifting a body wall, the method comprising the steps of:
   (a) providing first and second lifting rods carried by a lifting body, each lifting rod having a proximal portion, a distal portion, and a distal tip on the distal portion;
   (b) positioning the lifting rods for simultaneous insertion through an opening in the body wall by positioning the distal portions of the lifting rods in substantially side by side relation;
   (c) after step (b), inserting the lifting rods through the opening and into a body cavity;
   (d) after step (c), pushing body tissue away from the lifting rods by inflating a balloon disposed around the lifting rods;

(e) after step (d), positioning the lifting rods in a lifting configuration by rotating the second lifting rod to pivot its distal portion away from the body wall and within the body cavity and then towards the body wall into a spaced relationship with the first lifting rod, to thereby increase the distance between at least a portion of the distal portions of the lifting rods and positioning the distal tips proximal to one another to define a lifting area between the lifting rods; and (f) applying a lifting force to the lifting rods.

13. The method of claim 12 wherein:

step (b) comprises the step of rotating the second lifting rod to pivot the distal portion of the second lifting rod into substantially side by side relation with the distal portion of the first lifting rod; and step (c) comprises the step of inserting the distal portions of the lifting rods through the opening and into the body cavity.

14. The method of claim 12 further comprising the step of deflating the balloon when the lifting rods are in the lifting configuration to form a membrane extending between the distal portions of the lifting rods.

15. A method of laparoscopically lifting an abdominal wall, the method comprising the steps of:

(a) providing first and second lifting rods, each lifting rod having an arcuate distal portion remote from a lifting body and a proximal portion mounted to the lifting body, the lifting rods having an insertion configuration and a lifting configuration;

(b) positioning the lifting rods in the insertion configuration by placing the arcuate distal portions of the lifting rods in a nested condition:

(c) after step (b), inserting the lifting rods through a puncture opening and into the abdominal cavity;

(d) after step (c), pushing abdominal tissue away from the lifting rods by inflating a balloon disposed around the lifting rods;

(e) after step (d), positioning the lifting rods in the lifting configuration by rotating at least one of the lifting rods relative to the other to space the arcuate distal portions of the rods and form a lifting area therebetween; and (f) applying a lifting force to the lifting rods.

16. The method of claim 15 further comprising the step of deflating the balloon when the lifting rods are in the lifting configuration to form a membrane extending between the arcuate distal portions of the lifting rods.

* * * * *